(12) United States Patent
Duchini et al.

(10) Patent No.: US 11,510,824 B2
(45) Date of Patent: Nov. 29, 2022

(54) ROTARY WELDING DEVICE AND RELATED METHOD

(71) Applicant: GDM S.p.A., Bologna (IT)

(72) Inventors: Andrea Duchini, Castelleone (IT); Aldo Fusar Poli, Offanengo (IT); Matteo Piantoni, Albino (IT); Gabriele Resmini, Vailate (IT); Marco Rosani, Vailate (IT); Maurizio Spatti, Sulzano (IT)

(73) Assignee: GDM S.P.A., Bologna (IT)

( * ) Notice: Subject to any disclaimer, the term of this patent is extended or adjusted under 35 U.S.C. 154(b) by 0 days.

(21) Appl. No.: 17/368,314

(22) Filed: Jul. 6, 2021

(65) Prior Publication Data

US 2022/0000677 A1     Jan. 6, 2022

(30) Foreign Application Priority Data

Jul. 6, 2020 (IT) .......................... 102020000016210

(51) Int. Cl.
  *A61F 13/15* (2006.01)
  *B29C 65/78* (2006.01)
  *B29C 65/00* (2006.01)

(52) U.S. Cl.
  CPC .. *A61F 13/15739* (2013.01); *A61F 13/15764* (2013.01); *B29C 65/7885* (2013.01); *B29C 66/83511* (2013.01)

(58) Field of Classification Search
  CPC ................................................ A61F 13/15739
  See application file for complete search history.

(56) References Cited

U.S. PATENT DOCUMENTS

| 4,305,240 A | * | 12/1981 | Grevich | ................ | B29C 66/849 53/550 |
| 2017/0027763 A1 | * | 2/2017 | Fujita | ..................... | B29C 66/431 |

FOREIGN PATENT DOCUMENTS

| EP | 3078479 A1 | 10/2016 |
| EP | 3088164 A1 | 11/2016 |
| WO | 2015098535 A1 | 7/2015 |

OTHER PUBLICATIONS

Italian Search Report dated Mar. 22, 2021 from counterpart Italian Patent Application No. 102020000016210.

* cited by examiner

*Primary Examiner* — Barbara J Musser
(74) *Attorney, Agent, or Firm* — Shuttleworth & Ingersoll, PLC; Timothy J. Klima

(57) ABSTRACT

A rotary device for welding a continuous web comprises a rotary unit rotating about a respective axis and welding units for welding the web mounted, angularly spaced, on the rotary unit. A movement device varies a radial position of the welding units. First and second supporting elements supporting the web are disposed, respectively, upstream and downstream of respective ones of the welding units, to keep the web tensioned when the respective welding unit is at an operating position. The first and second supporting elements are supported by a load-bearing structure connected to the welding units in such a way that a radial movement of the welding units corresponds to a movement of the first and second supporting elements towards and away from the axis.

14 Claims, 4 Drawing Sheets

ROTARY WELDING DEVICE AND RELATED METHOD

This application claims priority to Italian Patent Application 102020000016210 filed Jul. 6, 2020, the entirety of which is incorporated by reference herein.

BACKGROUND OF THE INVENTION

This invention relates to a rotary welding device and to the related method.

In particular, the device according to this invention is configured to weld a continuous web along a direction transverse to the web feed direction according to a predetermined weld spacing.

For example, the device of this invention is configured to weld a continuous web to make absorbent articles or diapers, in particular to weld the side gathers of diaper pants.

In other embodiments, the device of this invention is configured for welding a continuous web for making packages for food and confectionery products such as chocolates or candies; beverage bottles and brick packs; pouches containing solid, liquid and semi-solid food products; products of the tobacco industry, products of the cosmetic industry, products of the pharmaceutical industry and products of the personal and home care industry.

In particular, the continuous web can be used to make packs or pouches for containing liquid or solid products.

Prior art apparatuses for welding absorbent articles typically comprise a rotary part on whose peripheral surface is placed the continuous web of absorbent articles to be welded.

A plurality of welding units are configured to weld the continuous web while the rotary part rotates through a predetermined circular arc.

The welding units are angularly spaced from each other about the axis of rotation of the rotary part.

The angular distance between one welding unit and the welding unit adjacent to it determines the weld spacing of the continuous web.

With reference to the continuous web, the weld spacing is defined by the linear distance between two distinct welds, one after the other in the longitudinal direction of extension of the web.

To optimize costs, there is a growing need to use the same rotary welding device to make different product formats by varying the weld spacing.

In order to vary the weld spacing of the device, it is necessary to vary the radial position of the welding units relative to the axis of rotation of the rotary element, in such a way as to determine a working circumference along which a desired weld spacing is obtained.

Varying the working circumference means varying the circular arc between each welding unit and the welding unit adjacent to it. The elements that support the continuous web must be disposed along that circular arc to ensure tensioning the portion of the web that will be welded by a respective welding unit.

In this context, the need was felt to develop elements for supporting the continuous web which are capable of responding to the variation in the working circumference without the operator having to intervene manually, avoiding the need to remove and reassemble parts manually and thus speeding up operations and ensuring the portions of the continuous web to be welded are correctly tensioned.

In effect, it should be borne in mind that when parts are removed manually during a format changeover performed manually, the continuous web disposed on the supporting elements must be cut and, after reassembling the parts, the continuous web must be wound onto the supporting elements once again.

In practice, the work involved makes this an extremely time-consuming operation.

As regards varying the working circumference, the need is felt to be able to vary this circumference uninterruptedly in order to be able to make standard and non-standard formats.

SUMMARY OF THE INVENTION

To meet this need, a rotary device is provided for welding a continuous web, preferably for making absorbent articles or for making pouches to contain liquid or solid products, comprising a rotary means rotating about a respective axis of rotation, a plurality of welding units for welding the continuous web and mounted on the rotary means in such a way as to be angularly spaced from each other.

It should be noted that the angular distance between the welding units defines a weld spacing.

Each welding unit is configured to pass from a non-operating position to an operating position and vice versa, during rotation of the rotary means.

Movement means are configured to vary the radial position of the welding units by moving them towards or away from the axis of rotation of the rotary means.

Varying the radial position of the welding unit allows varying the weld spacing of the continuous web.

A first supporting element and a second supporting element for supporting the continuous web, disposed, respectively, upstream and downstream of the same welding unit with reference to the rotation direction of the rotary means, keep the continuous web tensioned when the welding unit is at the operating position.

The first supporting elements and the second supporting elements associated with respective welding units are supported by a load-bearing structure that extends around the axis of rotation of the rotary means.

The load-bearing structure is connected to the welding units in such a way that a radial movement of the welding units corresponds to a movement of the first supporting elements and of the second supporting elements towards and away from the axis of rotation of the rotary means.

Advantageously, the simultaneous movement between the welding units and the supporting elements of the continuous web allows managing the format changeover of the rotary device without the aid of an operator.

At least one first supporting element and at least one second supporting element, associated with respective welding units are disposed, in pairs, between two respective welding units so that the continuous web, wrapped around the first supporting elements and the second supporting elements defines a polygonal perimeter whose length is variable as a function of the position of the first supporting elements and of the second supporting elements relative to the axis of rotation of the rotary means.

Advantageously, arranging the first supporting elements and of the second supporting elements in pairs between one welding unit and the next in the direction of rotation of the rotary means, allows disposing the continuous web along polylines which together define a polygonal perimeter; this allows managing the supporting elements for each position relative to the axis of rotation of the rotary means, without problems of space or interference between the supporting elements.

As shown in detail in FIGS. 3 and 4, the load-bearing structure comprises mounting bodies, each for at least one respective pair of at least one supporting element and one second supporting element, and connecting bodies, each of which connects the load-bearing structure to a respective welding unit.

Advantageously, the connecting bodies that connect the load-bearing structure to the welding units allow the entire load-bearing structure to be moved when the welding units are moved.

The mounting bodies are movably coupled to respective connecting bodies which are distinct from each other.

Each mounting body is movable towards and away from the respective connecting body.

Advantageously, each mounting body can pass from an initial position of minimum length to a final position of maximum length; that way, the first supporting elements and the second supporting elements can be positioned at a minimum position closest to, and a maximum position furthest from, the axis of rotation of the rotary means so as to be able to support the continuous web so the weld spacing ranges from a minimum length to a maximum length that is considerably longer than the minimum length.

In terms of weld spacing sizes obtainable, for example, for absorbent sanitary articles, this corresponds to a weld spacing for size S, the minimum length, and a weld spacing for size XL, the maximum length, with a total of at least four weld spacing lengths, corresponding to sizes S, M, L and XL.

For example, FIG. 1 shows the rotary device configured for the minimum length.

For example, FIG. 2 shows the rotary device configured for the maximum length.

Each mounting body comprises a respective first element and a respective second element, each connected to a respective connecting body.

Each first element and each second element of a respective mounting body comprises a respective first portion that is slidably linked to a respective connecting body of the load-bearing structure along a radial direction relative to the axis of rotation of the rotary means.

Advantageously, the sliding of the first element and of the second element of each mounting body allows translating the position of the respective first supporting elements and second supporting elements.

Each first element and each second element of a respective mounting body comprises a respective second portion that is slidably linked to the respective first portion along a circumferential direction relative to the axis of rotation of the rotary means, as shown in FIG. 4.

The first supporting element and the second supporting element are supported by the second portion of the first element and of the second element of the mounting body.

Advantageously, further sliding of the second portion and the first portion relative to each other allows the mounting body to expand radially to compensate for the welding units being spaced apart from each other during the radial movement away from each other.

Each mounting body supports a respective housing member for housing a respective first supporting element and a second supporting element.

The first supporting element and the second supporting element supported by the same housing member are associated with respective welding units which are distinct from each other.

The first supporting element and the second supporting element are disposed on the respective housing member at a fixed distance; more specifically, they are disposed at a respective first end and second end of the housing member.

This fixed distance defines a side of constant length in the polygonal perimeters obtainable by the radial displacement of the housing members.

Each housing member is movably coupled to the respective mounting body of the load-bearing structure, specifically to the second portion of the respective first element and of the second element.

As shown in FIG. 5, the load-bearing structure is slidably linked to a mounting frame linked to the rotary means.

The first supporting element and the second supporting element are in the form of rollers, each rotating about a respective axis of rotation.

Advantageously, the roller structure allows defining a zone of contact with the continuous web along a line transverse to the longitudinal extension of the web, defining a respective corner of the polyline obtained by winding the web round the rollers.

Retaining means are provided to hold a portion of the continuous web not intended to be welded.

The retaining means comprise a first flexible element and a second flexible element which extend around the axis of rotation of the rotary means and between which the portion of the continuous web is disposed.

Advantageously, the first flexible element and the second flexible element for retaining the continuous web portion not involved in welding facilitate maintenance and cleaning of the device if the continuous web should come out of the device.

This invention also relates to a rotary method for welding a continuous web, preferably for making absorbent articles or for making packs or pouches for containing liquid or solid products, wherein a plurality of welding units for welding the continuous web are disposed around a common axis of rotation in such a way as to be angularly spaced from each other.

The method comprises a step of conveying the continuous web around the axis of rotation and a step of welding the continuous web during the step of conveying the continuous web.

Depending on a weld spacing to be obtained, the method comprises a step of varying the radial position of the welding units and, at the same time, the position of the continuous web towards or away from the axis of rotation; the continuous web extends around the axis of rotation in such a way as to define a polygonal perimeter whose length is variable as a function of the radial position of the continuous web relative to the axis of rotation to be able to adapt to the variation in the radial position of the welding units.

BRIEF DESCRIPTION OF THE DRAWINGS

Further features of the invention and its advantages are more apparent in the following non-limiting description of some preferred embodiments of a rotary welding device, as illustrated schematically in the accompanying drawings, in which.

DESCRIPTION OF THE PREFERRED EMBODIMENTS

Figure 1:
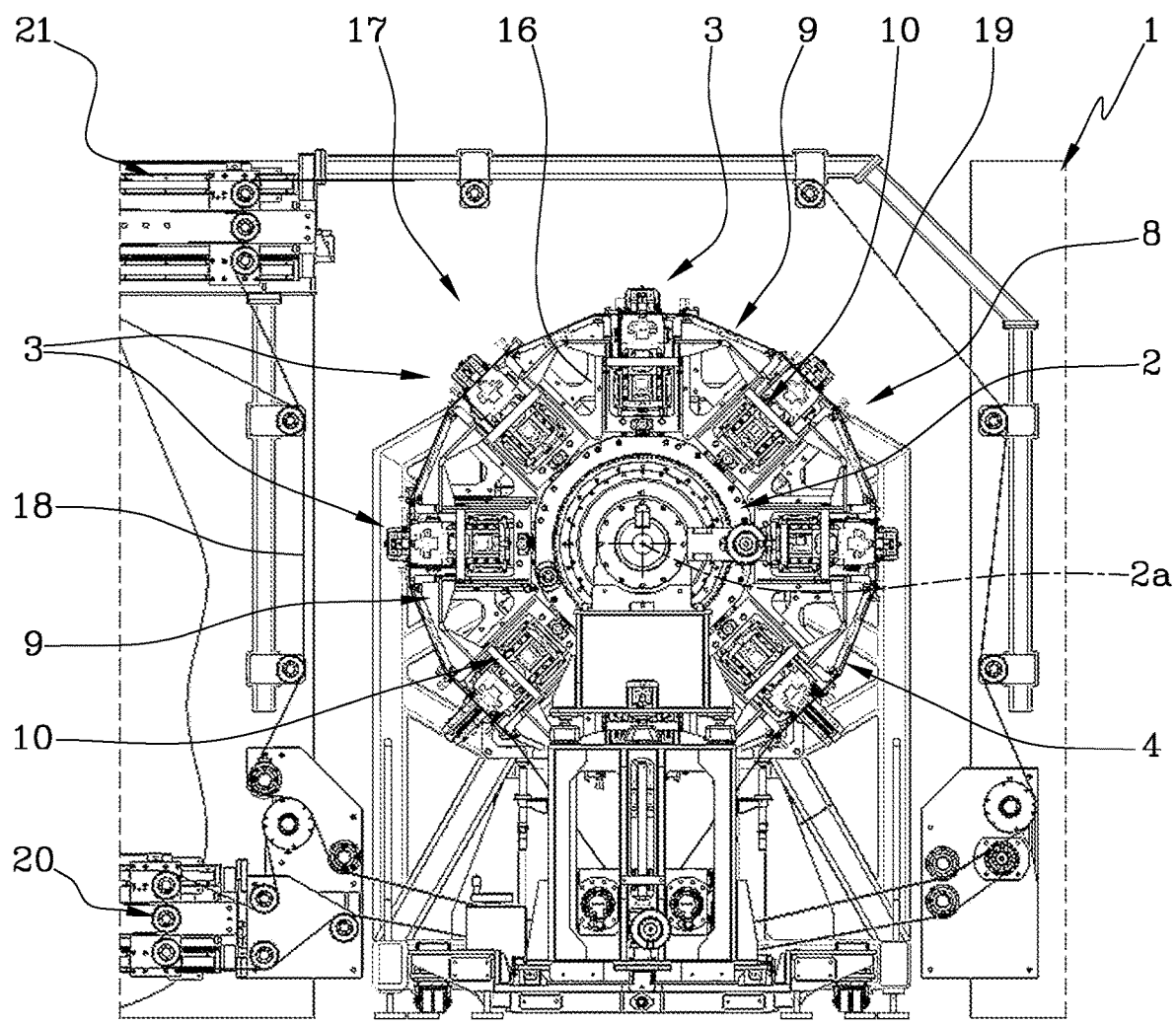
FIG. 1 is a schematic front view of a rotary welding device according to this invention at a position of minimum length.
Figure 2:
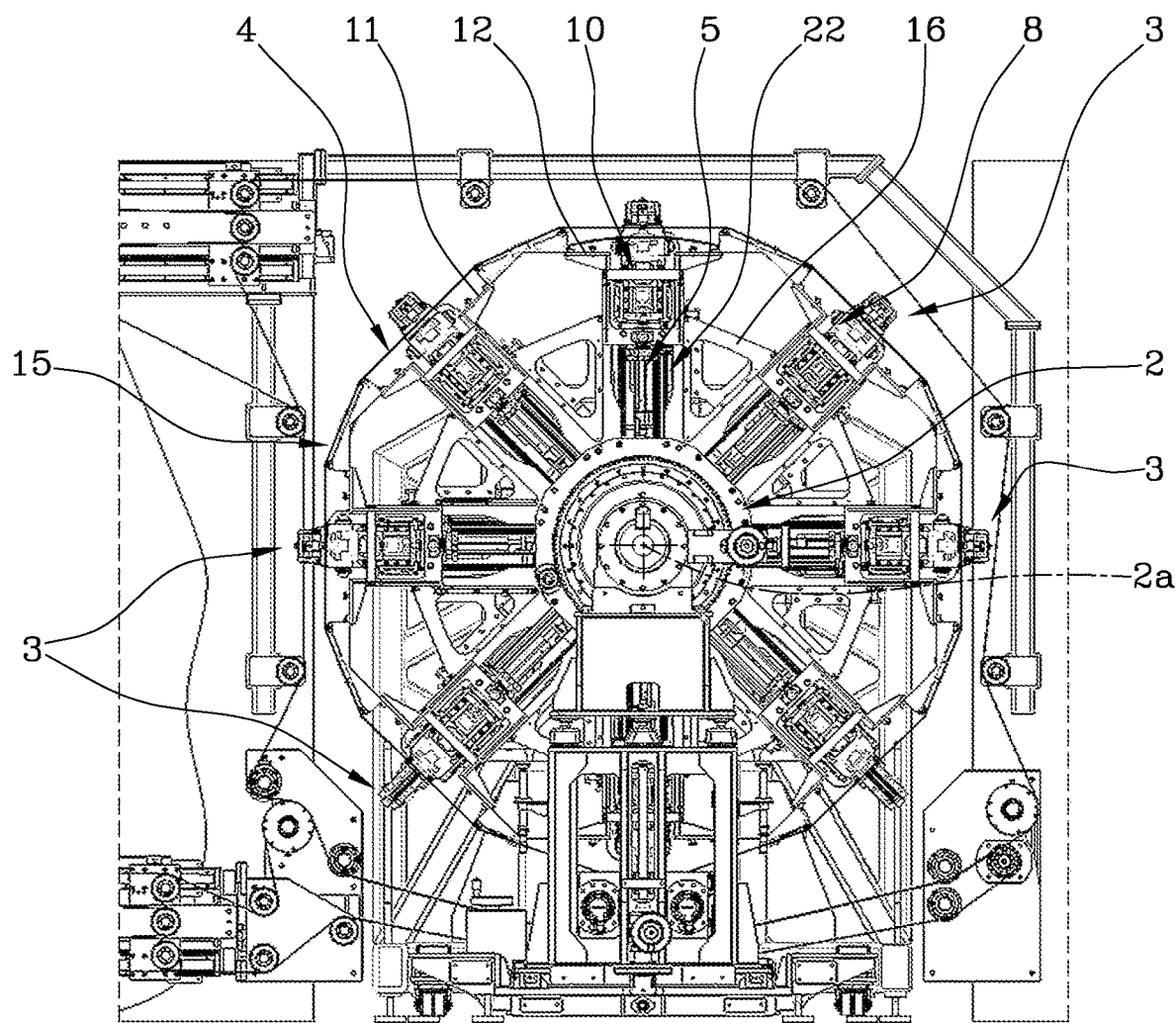
FIG. 2 is a schematic front view of a rotary welding device according to this invention at a position of maximum length.
Figure 3:
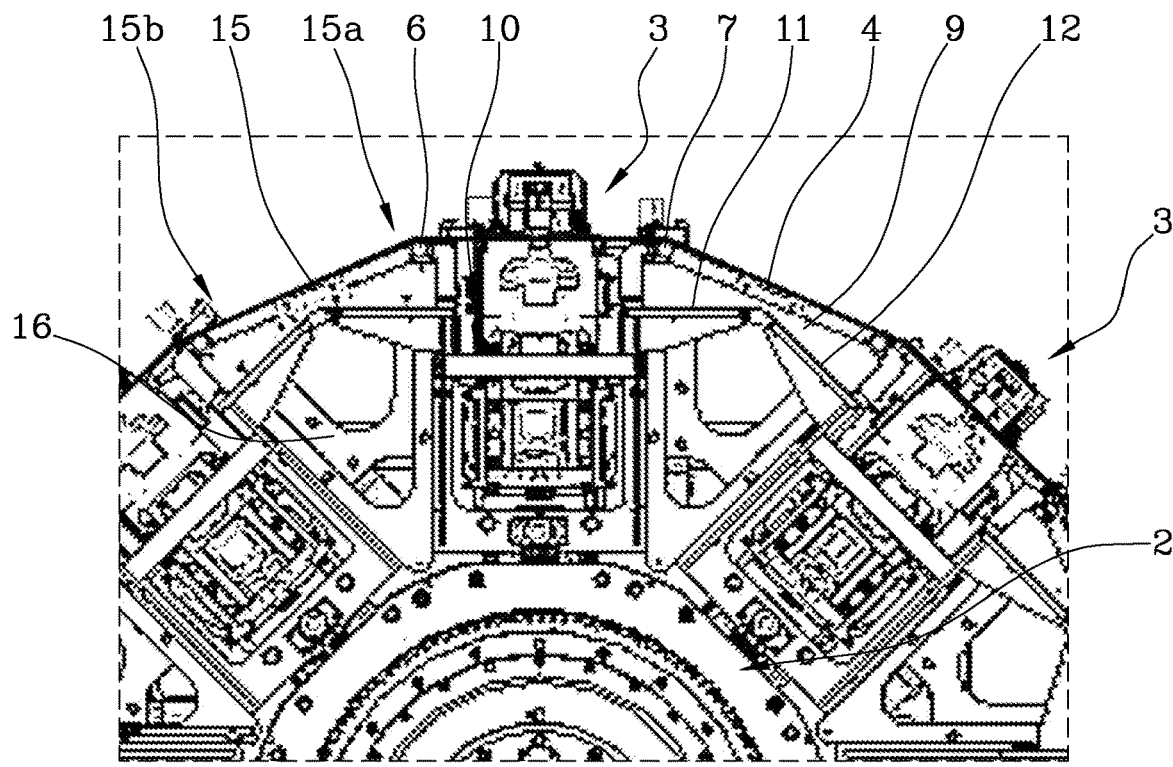
FIG. 3 shows an enlarged detail from FIG. 1.
Figure 4:
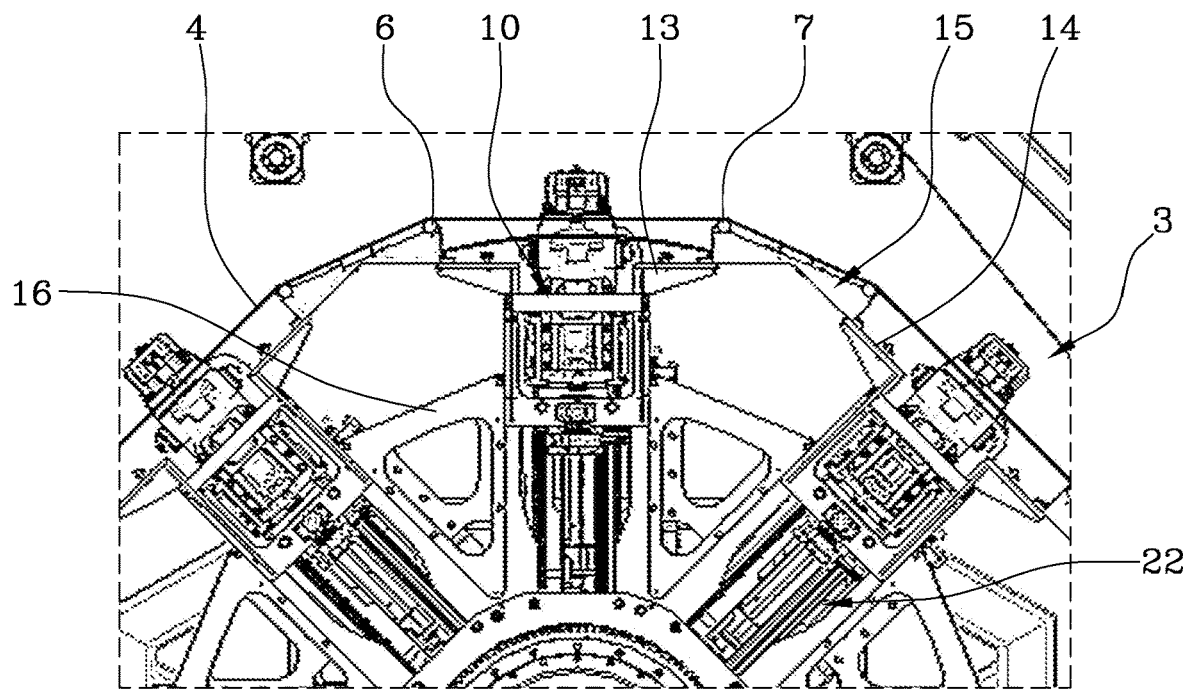
FIG. 4 shows an enlarged detail from FIG. 2.
Figure 5:
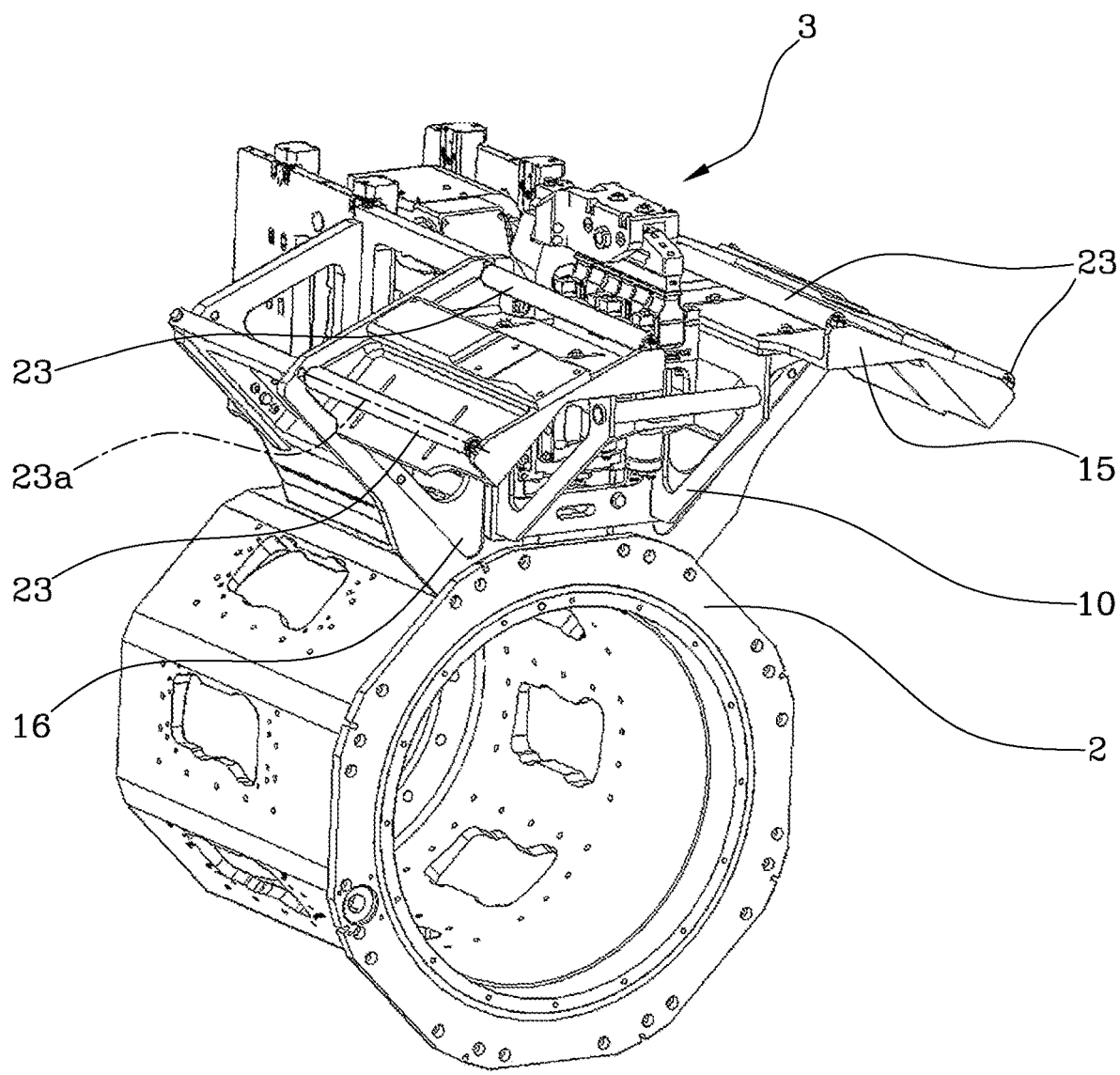
FIG. 5 shows a schematic perspective view of a detail of the rotary welding device, with some parts cut away in order to better illustrate others.

The reference numeral 1 denotes a rotary device for welding a continuous web 4 according to this invention.

Preferably, the rotary welding device 1 makes absorbent articles or parts thereof, or pouches for containing liquid or solid products.

The rotary device 1 comprises a rotary means 2 rotating about a respective axis of rotation 2a, a plurality of welding units 3 for welding the continuous web 4 and mounted on the rotary means 2 in such a way as to be angularly spaced from each other.

Preferably, the rotary means 2 comprises a cylindrical drum mounted on a shaft that rotates about the axis of rotation 2a.

Each welding unit 3 is configured to pass from a non-operating position to an operating position and vice versa, during rotation of the rotary means 2.

With reference to their rotation about the axis of rotation 2a, the welding units 3 pass from the non-operating position to the operating position in an arc of the working circumference.

The length of the arc of the working circumference is a function of the time needed to make the weld on the continuous web 4.

Movement means 5 are configured to vary the radial position of the welding units 3 by moving them towards or away from the axis of rotation 2a of the rotary means 2.

In other words, the movement means 5 move the welding units 3 in translation towards or away from the axis of rotation 2a of the rotary means 2.

The movement means 5 move all the welding units 3 towards or away from the axis of rotation 2a of the rotary means 2 simultaneously.

With reference to each welding unit 3, at least one first supporting element 6 and at least one second supporting element 7 for supporting the continuous web 4 are disposed, respectively, upstream and downstream of the welding unit 3 in the rotation direction of the rotary means 2.

The first supporting element 6 and the second supporting element 7 are in the form of rollers 23, each rotating about a respective axis of rotation 23a.

The supporting element 6 and the second supporting element 7 allow keeping the continuous web 4 tensioned when the welding unit 3 is at the operating position.

The first supporting elements 6 and the second supporting elements 7, associated with the respective welding units 3, are supported by a load-bearing structure 8 which is connected to the welding units 3.

A radial movement of the welding units 3 corresponds to a movement by the load-bearing structure 8 to move the first supporting elements 6 and the second supporting elements 7 towards and away from the axis of rotation 2a of the rotary means 2.

The load-bearing structure 8 allows simultaneously moving all the welding units 3 together with the first supporting elements 6 and the second supporting elements 7 which support the continuous web 4, so as to perform a format changeover operation without the aid of the operator.

The first supporting elements 6 and the second supporting elements 7, associated with the respective welding units 3, are disposed in pairs between two respective welding units 3.

That way, the continuous web 4, wrapped around the first supporting elements 6 and the second supporting elements 7, defines a polygonal perimeter whose length is variable as a function of the position of the first supporting elements 6 and of the second supporting elements 7 relative to the axis of rotation 2a of the rotary means 2.

Advantageously, the polygonal configuration allows making the function of supporting the continuous web 4 along the minimum and maximum polygonal length independent of the size of the first supporting elements 6 and second supporting elements 7.

The load-bearing structure 8 comprises mounting bodies 9 for mounting the first supporting elements 6 the second supporting elements 7.

Each mounting body 9 supports a respective pair of at least one first supporting element 6 and one second supporting element 7.

The load-bearing structure 8 comprises a plurality of connecting bodies 10, each of which connects the load-bearing structure 8 to a respective welding unit 3.

To be able to pass from a configuration of minimum length to a configuration of maximum length, the mounting bodies 9 are movably coupled to respective connecting bodies 10 which are distinct from each other.

Each mounting body 9 is movable towards and away from the respective connecting body 10.

In other words, each mounting body 9 is movable in translation towards and away from the respective connecting body 10.

Each mounting body 9 comprises a respective first element 11 and a respective second element 12, connected to a respective connecting body 10.

Each first element 11 and each second element 12 of a respective mounting body 9 comprises a respective first portion 13 slidably linked to a respective connecting body 10 of the load-bearing structure 8 along a radial direction towards and away from the axis of rotation 2a of the rotary means 2.

In other words, the first portion 13 of each first element 11 and each second element 12 moves in translation relative to the connecting body 10 of the load-bearing structure 8 towards and away from the axis of rotation 2a of the rotary means 2.

Each first element 11 and each second element 12 of a respective mounting body 9 comprises a respective second portion 14 slidably linked to the respective first portion 13 along a circumferential direction relative to the axis of rotation 2a of the rotary means 2 so that the second portion 14 of the first element 11 and the second portion 14 of the second element 12 move towards and away from each other.

The first supporting element 6 and the second supporting element 7 are supported by the second portion 14 of the first element 11 and of the second element 12 of the mounting body 9.

Each mounting body 9 supports a respective housing member 15 for housing a respective first supporting element 6 and a second supporting element 7.

More specifically, the first supporting element 6 and the second supporting element 7 supported by the same housing member 15 are associated with respective welding units 3 which are distinct from each other.

The first supporting element 6 and the second supporting element 7 are disposed on the respective housing member 15 at a fixed distance; more specifically, they are disposed at a respective first end 15a and second end 15b of the housing member 15.

Each housing member 15 is movably coupled to the respective mounting body 9 of the load-bearing structure 8, specifically to the second portion 14 of the respective first element 11 and of the second element 12.

The load-bearing structure 8 is slidably linked to a mounting frame 16 linked to the rotary means 2.

The mounting frame 16 comprises a plurality of guides 22 along which the load-bearing structure 8 slides.

The rotary welding device 1 comprises retaining means 17 for holding a portion of the continuous web 4 not intended to be welded.

The retaining means 17 comprise a first flexible element 18 and a second flexible element 19 which extend around the axis of rotation 2a of the rotary means 2 and between which the portion of the continuous web 4 that will not be welded is disposed.

In order to adapt the length of the first flexible element 18 and of the second flexible element 19 as a function of the variation in the position of the welding units 3 of the respective first supporting elements 6 and second supporting elements 7 relative to the axis of rotation 2a of the rotation means 2, first tensioning means 20 and second tensioning means 21 are configured to vary the length of the first flexible element 18 and of the second flexible element 19, respectively.

The invention also has for an object a rotary method for welding a continuous web, preferably for making absorbent articles or for making pouches for containing liquid or solid products, wherein a plurality of welding units 3 for welding the continuous web 4 are disposed around a common axis of rotation 2a in such a way as to be angularly spaced from each other.

The method comprises a step of conveying the continuous web 4 around the axis of rotation 2a and a step of welding the continuous web 4 during the step of conveying the continuous web 4.

Depending on a weld spacing to be obtained, the method comprises a step of varying the weld spacing comprising a step of varying the radial position of the welding units 3 and, at the same time, the position of the continuous web 4 towards or away from the axis of rotation 2a.

The step of varying the position of the continuous web 4 comprises disposing the continuous web 4 around the axis of rotation 2a in such a way as to define a polygonal perimeter whose length is variable as a function of the radial position of the continuous web 4 relative to the axis of rotation 2a so as to be able to adapt to the variation in the radial position of the welding units 3.

What is claimed is:

1. A rotary device for welding a continuous web, comprising
    a rotary drum rotating about a respective axis of rotation,
    a plurality of welding units for welding the continuous web and mounted on the rotary drum in such a way as to be angularly spaced from each other, each welding unit being configured to pass from a non-operating position to an operating position, and vice versa, during the rotation of the rotary drum;
    a movement mechanism configured to simultaneously vary radial positions of the welding units by simultaneously radially moving the welding units towards or away from the axis of rotation of the rotary drum;
    for each of the welding units, a first supporting element and a second supporting element connected thereto for supporting the continuous web and disposed, respectively, upstream and downstream of the each of the welding units with reference to a rotation direction of the rotary drum, to keep the continuous web tensioned when the each of the welding units is at the operating position;
    the first supporting elements and the second supporting elements connected with the welding units being supported by a load-bearing structure connected to the welding units in such a way that the simultaneously radially moving the welding units also causes simultaneously radially moving the first supporting elements and the second supporting elements towards and away from the axis of rotation of the rotary drum; and
    one of the first supporting elements and one of the second supporting elements are disposed, in pairs, between two adjacent ones of the welding units so that the continuous web, wrapped around the first supporting elements and the second supporting elements, defines a polygonal perimeter having a length that is variable as a function of radial positions of the first supporting elements and of the second supporting elements relative to the axis of rotation of the rotary drum.

2. The rotary device according to claim 1, wherein the load-bearing structure comprises mounting bodies, each for a respective pair of the first supporting elements and the second supporting elements, and connecting bodies, each of which connects the load-bearing structure to one of the welding units.

3. A rotary device for welding a continuous web, comprising
    a rotary drum rotating about a respective axis of rotation,
    a plurality of welding units for welding the continuous web and mounted on the rotary drum in such a way as to be angularly spaced from each other, each welding unit being configured to pass from a non-operating position to an operating position, and vice versa, during the rotation of the rotary drum;
    a movement mechanism configured to simultaneously vary radial positions of the welding units by simultaneously radially moving the welding units towards or away from the axis of rotation of the rotary drum;
    for each of the welding units, a first supporting element and a second supporting element connected thereto for supporting the continuous web and disposed, respectively, upstream and downstream of the each of the welding units with reference to a rotation direction of the rotary drum, to keep the continuous web tensioned when the each of the welding units is at the operating position;
    the first supporting elements and the second supporting elements connected with the welding units being supported by a load-bearing structure connected to the welding units in such a way that the simultaneously radially moving the welding units also causes simultaneously radially moving the first supporting elements and the second supporting elements towards and away from the axis of rotation of the rotary drum;
    the load-bearing structure comprising mounting bodies, each for a respective pair of the first supporting elements and the second supporting elements, and connecting bodies, each of which connects the load-bearing structure to one of the welding units; and
    wherein the mounting bodies are movably coupled to respective connecting bodies which are distinct from each other; each of the mounting bodies being movable towards and away from a respective one of the connecting bodies.

4. The rotary device according to claim 2, wherein each of the mounting bodies comprises a first element and a second element; the first element and the second element being connected to a respective one of the connecting bodies.

5. The rotary device according to claim 4, wherein the first element and the second element each comprises a first portion slidably linked to the respective one of the mounting bodies along a radial direction relative to the axis of rotation of the rotary drum.

6. The rotary device according to claim 5, wherein the first element and the second element each further comprises a second portion slidably linked to the first portion along a circumferential direction relative to the axis of rotation of the rotary drum; the first supporting element and the second supporting element being supported by the second portion of the first element and of the second element.

7. The rotary device according to claim 2, wherein each mounting body supports a housing member for housing the first supporting element and the second supporting element; the first supporting element and the second supporting element supported by the housing member being respectively connected to different ones of the welding units.

8. The rotary device according to claim 7, wherein the first supporting element and the second supporting element are disposed on the housing member at a fixed distance, at a respective first end and second end of the housing member.

9. The rotary device according to claim 7, wherein the housing member is movably coupled to the each mounting body, to the second portion of the first element and the second element.

10. The rotary device according to claim 1, wherein the load-bearing structure is slidably linked to a mounting frame linked to the rotary drum.

11. The rotary device according to claim 1, wherein the first supporting element and the second supporting element are rollers, each rotatable about a respective axis of rotation.

12. The rotary device according to claim 1, and further comprising a retaining device configured to hold a portion of the continuous web not intended to be welded; the retaining device including a first flexible element and a second flexible element which extend around the axis of rotation of the rotary drum and between which the portion of the continuous web is disposed.

13. A rotary method for welding a continuous web, comprising:
    providing a plurality of welding units for welding the continuous web disposed around a common axis of rotation in such a way as to be angularly spaced from each other;
    conveying the continuous web around the axis of rotation and a step of welding the continuous web during the step of conveying the continuous web;
    depending on a weld spacing to be obtained, varying the weld spacing by simultaneously varying radial positions of the welding units and the continuous web by simultaneously radially moving the welding units and the continuous web towards or away from the axis of rotation; the step of varying the radial positions of the welding units being carried out at a same time as the step of varying the radial position of the continuous web; and
    the step of varying the radial position of the continuous web comprising disposing the continuous web around the axis of rotation in such a way as to define a polygonal perimeter having a length that is variable as a function of the radial position of the continuous web relative to the axis of rotation to adapt to the radial position variation of the welding units.

14. A machine for making absorbent articles or for making packs or pouches for containing liquid or solid products, the machine comprising the rotary device according to claim 1.

* * * * *